United States Patent [19]

Kawamoto et al.

[11] Patent Number: 4,520,126
[45] Date of Patent: May 28, 1985

[54] CATALYST COMPOSITION SUITABLE FOR THE DIMERIZATION OR CODIMERIZATION OF ALPHA-OLEFINS

[75] Inventors: Keiji Kawamoto, Hiroshima; Keigo Kato, Yono; Takahiro Aida, Niitsu, all of Japan

[73] Assignee: Mitsui Petrochemical Industries, Ltd., Tokyo, Japan

[21] Appl. No.: 453,959

[22] Filed: Dec. 28, 1982

[30] Foreign Application Priority Data

Dec. 28, 1981 [JP] Japan .................................. 56-209969
Dec. 28, 1981 [JP] Japan .................................. 56-209971

[51] Int. Cl.³ ........................ B01J 27/20; B01J 23/04; C07C 11/10; C07C 21/24
[52] U.S. Cl. .................................. 502/184; 502/174; 585/516
[58] Field of Search ............................... 502/174, 184

[56] References Cited

U.S. PATENT DOCUMENTS 3,216,947 11/1965 Wilkes .................................. 252/192
3,291,752 12/1966 Keith et al. ........................... 502/174
3,758,416 9/1973 Forni .................................... 252/447

FOREIGN PATENT DOCUMENTS 47-2602 1/1972 Japan ................................... 585/516
7116200 5/1972 Netherlands ......................... 585/516

Primary Examiner—P. E. Konopka
Attorney, Agent, or Firm—Wenderoth, Lind & Ponack

[57] ABSTRACT

A catalyst composition consisting essentially of a molded article comprising an anhydrous inorganic potassium compound and metallic sodium and metallic potassium dispersed on the surface of the molded article, said molded article further containing 0.7 to 3% by weight, based on the weight of the inorganic potassium compound, of elemental carbon, the atomic ratio of metallic sodium to metallic potassium being in the range of from 20:80 to 90:10. This catalyst composition is useful for the dimerization or codimerization of alpha-olefins.

9 Claims, No Drawings

CATALYST COMPOSITION SUITABLE FOR THE DIMERIZATION OR CODIMERIZATION OF ALPHA-OLEFINS

This invention relates to a novel catalyst composition. More specifically, it relates to a catalyst composition having high activity and a long active lifetime which is composed of an anhydrous inorganic potassium compound as a base and metallic sodium and metallic potassium dispersed thereon, and to the use of the aforesaid catalyst composition in the dimerization or codimerization of alpha-olefin.

Many basic catalysts have previously been suggested for the dimerization or codimerization of alpha-olefins to produce the corresponding dimers or codimers. These catalysts, however, have proved to be not entirely satisfactory for commercial practice because they have low activity or do not have sufficiently high selectivity to the desired product, or have a short lifetime even when having high initial activity.

For example, U.S. Pat. Nos. 3,291,752 and 3,424,814 disclose that a catalyst composed of anhydrous potassium carbonate and elemental sodium dispersed thereon is used in the dimerization or codimerization of alpha-olefins. Japanese Patent Publication No. 22474/1967 discloses a catalyst composition for the dimerization or codimerization of lower alpha-olefins, which is composed of dried pellets of potassium carbonate containing 0.5% by weight of graphite as a binder and metallic sodium dispersed thereon. Japanese Laid-Open Patent Publication No. 14533/1980 discloses a catalyst for the dimerization or codimerization of alpha-olefins, which is composed of a granula anhydrous potassium compound and supported thereon a powdery anhydrous potassium compound and metallic sodium. These catalysts, however, do not have sufficiently high activity and/or have a short active lifetime, and are not entirely satisfactory for industrial application.

It is an object of this invention therefore to provide a novel catalyst composition which has high catalytic activity and a long active lifetime and is suitable for the dimerization or codimerization of alpha-olefins.

Another object of this invention is to provide a process for dimerizing or codimerizing an alpha-olefin using the aforesaid catalyst composition, particularly for producing 4-methyl-1-pentene by dimerizing propylene.

Thus, according to this invention, there is provided a catalyst composition consisting essentially of a molded article comprising an anhydrous inorganic potassium compound, and metallic sodium and metallic potassium dispersed on the surface of the molded article, said molded article further containing 0.7 to 3% by weight, based on the weight of the inorganic potassium compound, of elemental carbon, the atomic ratio of metallic sodium to metallic potassium being in the range of from 20:80 to 90:10.

The molded article constituting the catalyst composition of this invention is composed mainly of an anhydrous inorganic potassium compound and further includes elemental carbon. It is critical that the amount of the elemental carbon in the molded article should be in the range of 0.7 to 3% by weight based on the weight of the inorganic potassium compound. It has been unexpectedly found in accordance with this invention that the inclusion of 0.7% by weight or more of elemental carbon in the molded article extends the life of the resulting catalyst composition much longer than in the case of adding it in a small amount of about 0.5% by weight as a binder as disclosed in the above-cited Japanese Patent Publication No. 22474/1967, and markedly increases its activity in the dimerization and codimerization of alpha-olefins. It has also been found that this effect is the greatest when the content of elemental carbon is in the range of about 0.9 to 1.5% by weight, and does not further increase even if the content of elemental carbon is increased, and that when its content exceeds 3% by weight, the strength of the molded article after compression molding is reduced and the life of the catalyst composition is decreased.

The preferred amount of elemental carbon is in the range of 0.8 to 2% by weight, more preferably 0.9 to 1.5% by weight, based on the weight of the inorganic potassium compound in the molded article.

Examples of the elemental carbon which can be incorporated in the molded article in order to obtain the aforesaid effect are graphite and carbon black. Graphite is preferred. The elemental carbon can be mixed in the form of a fine powder having an average particle diameter of generally not more than 200 microns, preferably not more than 50 microns, with the inorganic potassium compound.

The inorganic potassium compound may be any of the potassium compounds which have heretofore been used in catalysts of this kind. Examples include potassium carbonate, potassium silicate, potassium sulfate, potassium fluoride, potassium chloride, and potassium bromide. Potassium carbonate is preferred. The bulk density of the powder of the anhydrous potassium compound constituting the molded article formed by compression molding is usually not more than 1.0 g/ml calculated by the method described below before the compression molding. Use of the anhydrous potassium compound having a bulk density of 0.9 to 0.5 g/ml as a component of the compression-molded article is preferred because it increases the activity and life of the catalyst and the selectivity to the dimerized product.

The inorganic potassium compound is mixed in powder form uniformly with the elemental carbon powder, and the mixture can be compression-molded. It has surprisingly been found in accordance with this invention that the life of the catalyst composition can be further prolonged, and its activity can be further increased, by using a special inorganic potassium compound powder which has an average particle diameter in the range of 150 to 600 microns, preferably 200 to 600 microns, and a selected specified particle size distribution such that it contains 1 to 15% by weight, preferably 2 to 10% by weight, of particles having a particle diameter smaller than 100 microns and 1 to 20% by weight, preferably 2 to 15% by weight, of particles having a particle diameter exceeding 600 microns. Accordingly, a catalyst composition comprising a molded article prepared from an inorganic potassium compound powder having such a specified particle size distribution is especially preferred in this invention.

Mixing of the inorganic potassium compound powder with the elemental carbon can usually be effected by ordinary methods. The resulting mixture is then compression-molded by a conventional compression-molding device such as a tableting machine, a compression-molding machine, or a pelletizer to form a molded article of any suitable form such as granules, tablets, pellets, solid cylinders, hollow cylinders, or spheres. Desirably, such a molded article generally has a particle diameter of at least 0.5 mm, preferably 1 to 10 mm. The compression molded can usually be carried out at room temperature, but at times, at an elevated temperature of up to about 100° C. The suitable pressure which can be applied during compression molding is generally in the range of 10 to 1,000 kg/cm², preferably 100 to 500 kg/cm².

Advantageously, the resulting molded article may have a pore volume ratio of 22 to 38%, preferably 26 to 33%, and a compression strength in the range of 1.5 to 15 kg/cm².G, preferably 2 to 10 kg/cm².G.

It is further critical that the molded article should be substantially anhydrous. That is, the molded article should not contain water in an amount exceeding generally 1,000 ppm, preferably 100 ppm. Hence, the inorganic potassium compound as a main component of the molded article should also be anhydrous. It should be understood that water, as used with regard to the inorganic potassium compound, denotes not only adhering water but also water of crystallization. It is advantageous that when the molded article contains water in an amount exceeding the aforesaid upper limit, it is dried by an ordinary method, for example by using an electric dryer or a steam dryer, to render it substantially anhydrous.

Metallic sodium and metallic potassium are deposited on the surface of the resulting molded article composed mainly of the inorganic potassium compound. The atomic ratio of metallic sodium to metallic potassium is adjusted to 20:80 to 90:10. If the Na/K atomic ratio is lower than 20:80, the initial activity of the resulting catalyst becomes high but is markedly decreased with time, and its life is shortened. If the Na/K atomic ratio is higher than 90:10, the catalytic activity and the selectivity to the dimerization or codimerization product are reduced, and the induction period required until the catalyst exhibits its highest activity is markedly prolonged. The preferred atomic ratio of metallic sodium to metallic potassium to be deposited on the molded article is preferably from 30:70 to 85:15, more preferably from 35:65 to 75:25.

The total amount of metallic sodium and metallic potassium on the molded article is generally 0.5 to 10% by weight, preferably 1 to 5% by weight, based on the weight of the inorganic potassium compound in the molded article.

As required, the molded article used in this invention may also have deposited thereon another catalytically active or inactive component in addition to metallic sodium and metallic potassium. Specific examples of the other components that can be deposited are anhydrous inorganic alkali metal compounds such as potassium carbonate and sodium carbonate, and elemental carbon. The inorganic alkali metal compound can be deposited in an amount of not more than 5% by weight, preferably not more than 4% by weight, and the elemental carbon, in an amount of up to 2% by weight, preferably not more than 1% by weight, both based on the total amount of metallic sodium and potassium.

Deposition of metallic sodium and metallic potassium and as required the other components on the surface of the molded article can be performed by various methods known per se. Specifically, the following methods may be cited as examples.

(1) A method in which metallic sodium and the molded article, optionally together with the optional catalyst components such as an anhydrous inorganic alkali metal compound or an elemental carbon powder, are contacted with stirring in an inert gaseous atmosphere at an elevated temperature.

(2) A method in which an alloy of metallic sodium and metallic potassium and the molded article, optionally together with the other catalyst components, are contacted with stirring in an inert gaseous atmosphere at an elevated temperature.

In the methods (1) and (2), the heating temperature can be adjusted usually to about 150° C. to about 400° C., preferably to about 200° C. to about 350° C. Heating and stirring can be continued until the metallic sodium and potassium are deposited in the desired proportions on the surface of the granular molded article. The time required for this is approximately in the range of 0.5 to 10 hours.

When the molded article is contacted under heat with metallic sodium or the alloy of metallic sodium and potassium as above, an exchanging reaction of the alkali metals takes place between metallic sodium and the inorganic potassium compound in the molded article in the method (1) described above, whereby a part of metallic sodium is converted to an inorganic sodium compound and simultaneously metallic potassium is precipitated. Accordingly, in the aforesaid method, care must be taken so as to stop the alkali metal exchanging reaction when the desired atomic ratio of metallic sodium to metallic potassium is obtained. This point in time can be easily determined by one skilled in the art by performing a small-scale experiment.

In the catalyst composition prepared as above, metallic sodium and metallic potassium and optionally the other catalyst component are deposited on the surface of the molded article. Since the melting point of a mixture of metallic sodium and metallic potassium is about $-13°$ C. to about 98° C. depending upon the mixing ratio of Na and K, the deposited mixture of metallic sodium and potassium may sometimes be liquid.

As stated hereinabove, the catalyst composition provided by this invention exhibits superb catalytic activity and has a long active lifetime in the dimerization or codimerization of alpha-olefins, and can be used in an industrially advantageous manner as a catalyst for the dimerization or codimerization of alpha-olefins, especially the production of 4-methyl-1-pentene by the dimerization of propylene.

Known (co)dimerization catalysts for alpha-olefins have been used normally in a region where the conversion of alpha-olefins is high. These catalysts, however, suffer from the defect that the reduction of their catalytic activity is remarkable, and even when they are used at a lower conversion of alpha-olefins, the durability of their catalytic activity, and their selectivity to the (co)dimerized products cannot be so much improved. In contrast, the catalyst composition of this invention is characterized by the fact that the reduction of its catalytic activity is inhibited not only at a high conversion of alpha-olefins, but also to a marked degree at a low conversion of alpha-olefins, particularly less than 50%, and that the composition has a long catalyst life and exhibits a high selectivity to the (co)dimerized products.

Specific examples of the alpha-olefins which can be dimerized or codimerized by using the catalyst composition of this invention are lower alpha-olefins such as ethylene, propylene, 1-butene, isobutylene and 1-pentene. The catalyst composition of this invention is especially preferably applied to the production of 4-methyl- 1-pentene by the dimerization of propylene, the production of 4-methyl-1-pentene by the codimerization of 1-butene and ethylene, and the production of 2-methyl-1-pentene by the codimerization of isobutylene and ethylene. It can be especially advantageously used in the production of 4-methyl-1-pentene by the dimerization of propylene.

The dimerization or codimerization of alpha-olefins in the presence of the catalyst composition of this invention may be carried out by methods known per se, specifically by vapor phase or liquid phase methods under heat. The vapor phase methods are preferred. In the case of the vapor-phase methods, the reaction temperature may usually be 0° to 300° C., preferably 100° to 200° C. The reaction pressure may usually be atmospheric pressure to 200 kg/cm$^2$.G, preferably 20 to 150 kg/cm$^2$.G. The reaction can be carried out in a fixed bed or a fluidized bed. Preferably, the fixed bed system is used. When the reaction is carried out in the fixed bed, the liquid hourly space velocity (LHSV) of the alpha-olefin is usually 0.1 to 10 hr$^{-1}$, preferably 0.5 to 5 hr$^{-1}$. The unreacted alpha-olefin and the product are separated in a customary manner from the resulting reaction mixture after the termination of the reaction, and the unreacted alpha-olefin is recycled to the reaction.

The following examples illustrate the present invention more specifically. It should be understood that these examples in no way limit the scope of the present invention.

The properties of the molded articles and the catalyst compositions in these examples were measured as follows:

(1) Particle size distribution of the anhydrous potassium compound powder:

Standard sieves having opening sizes of 16 mesh to 200 mesh according to JIS standards were combined. To the top of the combined sieves was added 150 g of the anhydrous potassium compound powder, and the entire assembly was sealed up in a polyethylene bag. The combined sieves were then set in a Ro-Tap type vibratory sieve shaking device (Model 19-45, made by Kurihara Seisakusho Co., Ltd.), and shaken for 10 minutes at a shaking rate of 290 cycles/minute and a hammering rate of 156 cycles/minutes. After the shaking, the weight of the anhydrous potassium compound left on each of the sieves was measured, and its weight percentage was calculated. From an RRS (Rosin-Rammler) diagram prepared from these data, the average particle diameter of the anhydrous potassium compound was determined.

(2) Pore volume ratio of the molded article;

About 10 g of a molded article sample dried at 300° C. for 2 hours was used, and its specific gravity in mercury and carbon tetrachloride was measured at 40° C. The pore volume ratio, defined by the percentage of pore volumes in the entire volume of the molded article, was calculated from the following equation.

$$\text{Pore volume ratio (\%)} = \left(1 - \frac{D_{Hg} \times \rho_{Hg}}{D_{CCl_4} \times \rho_{CCl_4}}\right) \times 100$$

wherein $D_{Hg}$ is the specific gravity of the sample in mercury, $D_{CCl_4}$ is the specific gravity of the sample in carbon tetrachloride, $\rho_{Hg}$ is the density of mercury at 40° C., and $\rho_{CCl_4}$ is the density of carbon tetrachloride at 40° C.

(3) Contact of graphite in the molded article:

Water (100 ml) and 20 ml of methanol were added to 50 g of a molded article sample dried in advance at 300° C. for 2 hours, and the mixture was stirred for 20 minutes by a magnetic stirrer. The mixture was then further stirred for 30 minutes by an ultrasonicating washer. Graphite which was thus freed from the molded article was washed with water and dried at 100° C. for 2 hours, and its weight was measured. The weight percentage of the graphite based on the weight of the anhydrous potassium compound in the molded article was calculated.

(4) Proportion of deposited alkali metals:

Water (15 ml) was added to about 2 g of a precisely weighed catalyst composition in an atmosphere of nitrogen, and the amount of generated hydrogen gas was measured by a gas burette.

Let the temperature at the time of measurement be t (°C.), the pressure be P (mmHg), the partial pressure of water at t (°C.) be $P_{H_2O}$ (mmHg), the amount of gas generated be V (ml), the amount of the deposited alkali metal in M (g) of the measured catalyst composition be A (g), the carbon content of the catalyst be C (g), and the amount of the deposited alkali metal per 100 g of the anhydrous potassium compound be B (g-atoms), the A and B can be calculated from the following equations.

$$A = 9.71 \times \frac{(760 - P_{H_2O})}{(273 + t)} \times P \times V \times 10^{-7}$$

$$B = 4.35 \times \frac{A}{[M - (A + C)]}$$

On the other hand, 50 ml of anhydrous isopropyl alcohol was added to 2 g of the catalyst composition in an atmosphere of nitrogen, and the mixture was left to stand at room temperature for 1 hour. Then, the molded article as a carrier and other solids were separated centrifugally. The amounts of sodium alkoxide and potassium alkoxide dissolved in isopropyl alcohol were measured by atomic absoptiometry, and the Na/K ratio was calculated from the measured amounts of these compounds.

The amounts of Na and K per 100 g of the anhydrous potassium compound in the deposited alkali metal component constituting the catalyst composition were determined in accordance with the following equations from the amount B (g-atoms) of the deposited alkali metals per 100 g of the anhydrous potassium compound and the Na/K ratio determined as above.

$$\text{Amount of Na (g-atoms/100 g of anhydrous K compound)} = B \times \frac{(\text{Na/K})}{1 + (\text{Na/K})}$$

$$\text{Amount of K (g-atoms/100 g of anhydrous K compound)} = B \times \frac{1}{1 + (\text{Na/K})}$$

(5) Bulk density of the anhydrous potassium compound powder:

A funnel including a sample dropping port at its lower end and having an inside diameter of 26.5 mm at its lower end, an inside diameter at its upper end of 94 mm, a height of 100 mm and a capacity of 150 ml was fixed perpendicularly so that its height up to the sample dropping port at its lower end became 100 mm. A cylindrical receiver having an inside diameter of 39 mm, a height of 81 mm and a capacity of 98.0 ml was placed immediately below the sample dropping port of the funnel. The anhydrous potassium compound powder was put in the funnel, and the sample dropping port at its lower end was opened to let the sample powder fall into the receiver. The raised portion of the sample at the upper portion of the receiver was removed by scraping it horizontally. The weight of the sample remaining in the receiver was measured, and the bulk density of the sample was calculated.

(6) Other properties were measured by methods known in the art.

EXAMPLE 1

(1) Catalyst preparation

A powder of anhydrous potassium carbonate having an average particle diameter of 300 microns and containing 4.8% of particles having a particle diameter of less than 100 microns and 4.2% of particles having a particle diameter of more than 600 microns but not exceeding 1000 microns, and having a bulk density of 0.7 g/ml was mixed with 1.0% by weight of graphite having an average particle diameter of 8 microns. The mixture was tableted into cylindrical tablets having a diameter of 3 mm and a height of 3 mm.

The cylindrical tablets (97.5 g) were dried in a stream of nitrogen at 350° C. for 2 hours, and 2.5 g of sodium was added in an atmosphere of nitrogen. The mixture was stirred at 230° C. for 5 hours to prepare a catalyst composition. The properties of the cylindrical tablets and the catalyst composition are shown in Table 1.

(2) Dimerization

Propylene was dimerized using the catalyst composition prepared in (1) above. The catalyst composition was filled into a pressure-resistant vapor-phase reactor, and while maintaining the reactor at a pressure of 100 kg/cm$^2$.G and a temperature of 157° C., propylene was fed at a liquid hourly space velocity (LHSV) of 0.85 hr$^{-1}$ and continuously reacted. The conversion of propylene reached a maximum of 85% after the lapse of 5 hours, and then gradually decreased. The half life of the maximum activity, i.e. the time required until the maximum conversion of propylene decreased to half, was 1,800 hours. The content of 4-methyl-1-pentene in the resulting hexene fraction was 92%.

EXAMPLE 2

Propylene was dimerized by using the catalyst composition prepared in (1) of Example 1 in the same way as in Example 1, (2) except that the LHSV was adjusted to 2.70 hr$^{-1}$ and the reaction temperature was adjusted to 150° C. The results are shown in Table 1.

EXAMPLES 3 TO 9

Molded articles having the properties shown in Table 1 were produced by a tableting method using anhydrous potassium carbonate having the same particle size distribution as in Example 1, (1) except that at least one of the graphite content, pore volume ratio and compression strength was changed as shown in Table 1. Using these molded articles, catalyst compositions having the properties shown in Table 1 were prepared in the same way as in Example 1, (1). Propylene was dimerized under the same conditions as in Example 2 using the resulting catalyst compositions. The results are shown in Table 1.

EXAMPLES 10 TO 12

Molded articles having the properties shown in Table 1 in the form of cylindrical tablets 3 mm in diameter and 3 mm in height were produced by tableting in accordance with the method of Example 1, (1) by using a powder of anhydrous potassium carbonate having a bulk density of 1.1 g/ml and an average particle size of 450 microns and containing 0.51% by weight of particles having a particle diameter of less than 100 microns and 27.6% by weight of particles having a particle diameter of more than 600 microns but not exceeding 1,000 microns (a product of Nippon Soda Co., Ltd.).

Catalyst compositions having the properties shown in Table 1 were prepared from these molded articles in the same way as in Example 1, (1).

Propylene was dimerized by using these catalyst compositions under the same conditions as in Example 2. The results are shown in Table 1.

TABLE 1

| | Properties of anhydrous $K_2CO_3$ | | | Properties of the molded article as carrier | | | Deposited alkali metals (per 100 g of $K_2CO_3$) | | | |
|---|---|---|---|---|---|---|---|---|---|---|
| | Average | Particle size distribution | | Graphite con- | Pore | Compression | Na | | K | |
| Ex- ample | Particle diameter (microns) | less than 100 microns (%) | 600–1000 microns (%) | tent (g/100 g of $K_2CO_3$) | volume ratio (%) | strength (kg/cm$^2$ · G) | ($\times 10^{-2}$ g-atom) | (g-atom %) | ($\times 10^{-2}$ g-atom) | (g-atom %) |
| 1 | 300 | 4.8 | 4.2 | 1.0 | 32 | 3.4 | 6.3 | (58) | 4.6 | (42) |
| 2 | 300 | 4.8 | 4.2 | 1.0 | 32 | 3.4 | 6.3 | (58) | 4.6 | (42) |
| 3 | 300 | 4.8 | 4.2 | 1.0 | 29 | 4.8 | 5.9 | (55) | 5.0 | (45) |
| 4 | 300 | 4.8 | 4.2 | 1.5 | 33 | 3.0 | 5.2 | (47) | 5.7 | (53) |
| 5 | 300 | 4.8 | 4.2 | 2.0 | 34 | 3.8 | 5.2 | (47) | 5.7 | (53) |
| 6 | 300 | 4.8 | 4.2 | 1.2 | 35 | 2.1 | 6.6 | (57) | 5.1 | (43) |
| 7 | 300 | 4.8 | 4.2 | 1.2 | 32 | 2.5 | 5.9 | (50) | 5.9 | (50) |
| 8 | 300 | 4.8 | 4.2 | 0.9 | 32 | 3.4 | 6.3 | (58) | 4.6 | (42) |
| 9 | 300 | 4.8 | 4.2 | 0.75 | 32 | 3.4 | 6.3 | (58) | 4.6 | (42) |
| 10 | 450 | 0.5 | 27.6 | 1.0 | 32 | 3.4 | 6.2 | (57) | 4.8 | (43) |
| 11 | 450 | 0.5 | 27.6 | 1.5 | 33 | 3.0 | 5.2 | (50) | 5.3 | (50) |
| 12 | 450 | 0.5 | 27.6 | 2.0 | 34 | 3.8 | 4.7 | (47) | 5.3 | (53) |

| | Catalyst composition Deposited alkali metals (per 100% of $K_2CO_3$) | | | Dimerization reaction conditions | | | Catalytic activity | | |
|---|---|---|---|---|---|---|---|---|---|
| Ex- ample | Na/K atomic ratio | Deposited alkali metals (total) | | Temperature (°C.) | Pressure (kg/cm$^2$ · G) | LHSV (hr$^{-1}$) | Conversion (%) | Selectivity(*) (%) | Half life (hr) |
| | | ($\times 10^{-2}$ g-atom) | (g) | | | | | | |
| 1 | 1.4 | 10.9 | (3.2) | 157 | 100 | 0.85 | 85 | 92 | 1800 |
| 2 | 1.4 | 10.9 | (3.2) | 150 | 100 | 2.70 | 28 | 93 | >6000 |
| 3 | 1.2 | 10.9 | (3.3) | 150 | 100 | 2.70 | 26 | 92 | >6000 |

TABLE 1-continued

| | | | | | | | | |
|---|---|---|---|---|---|---|---|---|
| 4 | 0.9 | 10.9 | (3.4) | 150 | 100 | 2.70 | 29 | 93 | >6000 |
| 5 | 0.9 | 10.9 | (3.4) | 150 | 100 | 2.70 | 30 | 93 | >6000 |
| 6 | 1.3 | 11.7 | (3.5) | 150 | 100 | 2.70 | 26 | 92 | >6000 |
| 7 | 1.0 | 11.8 | (3.7) | 150 | 100 | 2.70 | 27 | 93 | >6000 |
| 8 | 1.4 | 10.9 | (3.2) | 150 | 100 | 2.70 | 27 | 93 | >6000 |
| 9 | 1.4 | 10.9 | (3.2) | 150 | 100 | 2.70 | 25 | 93 | >6000 |
| 10 | 1.3 | 11.0 | (3.3) | 150 | 100 | 2.70 | 23 | 92 | 5500 |
| 11 | 1.0 | 10.5 | (3.3) | 150 | 100 | 2.70 | 24 | 93 | 5500 |
| 12 | 0.9 | 10.0 | (3.1) | 150 | 100 | 2.70 | 24 | 93 | 5500 |

(*): Proportion of 4-methyl-1-pentene in the hexene fraction.

Comparative Example 1

The catalyst shown in Table 2 was prepared in the same way as in Example 1, (1) except that the conditions for sodium deposition were changed. Propylene was dimerized in the presence of this catalyst composition under the same conditions as in Example 2. The results are shown in Table 2.

Comparative Examples 2 to 4

The molded articles shown in Table 2 were produced by a tableting method using anhydrous potassium carbonate having the same particle size distribution as in Example 1, (1) except that the graphite content was changed to 0.5% by weight and the pore volume ratio and compression strength were changed as shown in Table 2. The catalysts having the properties shown in Table 2 were prepared by using these molded articles in accordance with the method of Example 1, (1).

Propylene was dimerized in the presence of these catalyst compositions under the same conditions as in Example 2. The results are shown in Table 2.

Comparative Example 5

The catalyst shown in Table 2 was prepared as in Example 1, (1) except that the graphite content of the carrier was changed to 0.5% by weight and sodium was deposited at 140° C. for 2 hours. Propylene was dimerized in the presence of this catalyst under the same conditions as in Example 2. The results are shown in Table 2.

Comparative Examples 6 and 7

Molded articles were produced by tableting as in Example 1, (1) using anhydrous potassium carbonate having the same particle size distribution and bulk density as in Example 1, (b 1) except that the graphite content was changed to 0.5% by weight and the pore volume ratio and compression strength were changed as shown in Table 2. The catalysts shown in Table 2 were prepared from the resulting molded articles in the same way as in Example 1, (1).

Propylene was dimerized in the presence of these catalyst compositions under the same conditions as in Example 2. The results are shown in Table 2.

Comparative Example 8

Cylindrical tablets having a diameter of 3 mm and a height of 3 mm containing 0.5% by weight of graphite were produced by tableting in the same way as in Example 1, (1) using anhydrous potassium carbonate having a bulk density of 1.1 g/ml and an average particle diameter of 450 microns and containing 0.5% of particles having a particle diameter of less than 100 microns and 27.6% of particles having a particle diameter of more than 600 microns but not exceeding 1,000 microns. The catalyst shown in Table 2 was prepared by using the resulting carrier in accordance with the method shown in Example 1, (b 1).

Propylene was dimerized in the presence of the resulting catalyst under the same conditions as in Example 2. The results are shown in Table 2.

Comparative Example 9

The catalyst shown in Table 2 was prepared by using the same anhydrous potassium carbonate as used in Example 10 and changing the conditions for depositing sodium in Example 10. Propylene was dimerized in the presence of the resulting catalyst under the same conditions as in Example 2. The results are shown in Table 2.

Comparative Example 10

The molded article as a carrier was produced by tableting as in Comparative Example 9 except that the graphite content of the carrier was changed to 4.0% by weight. The catalyst shown in Table 2 was prepared by using the resulting granular molded article in the same way as in Example 1, (1).

Propylene was dimerized in the presence of the resulting catalyst under the same conditions as in Example 2. The results are shown in Table 2.

TABLE 2

| | Catalyst Composition | | | | | | | | | |
|---|---|---|---|---|---|---|---|---|---|---|
| Comparative Example | Properties of anhydrous $K_2CO_3$ | | | Properties of the molded article as carrier | | | Deposited alkali metals (per 100 g of $K_2CO_3$) | | | |
| | Average Particle diameter (microns) | Particle size distribution | | Graphite content (g/100 g of $K_2CO_3$) | Pore volume ratio (%) | Compression strength (kg/cm$^2$ · G) | Na | | K | |
| | | less than 100 microns (%) | 600–1000 microns (%) | | | | ($\times 10^{-2}$ g-atom) | (g-atom %) | ($\times 10^{-2}$ g-atom) | (g-atom %) |
| 1 | 300 | 4.8 | 4.2 | 1.0 | 32 | 3.4 | 10.5 | (96) | 0.4 | (4) |
| 2 | 300 | 4.8 | 4.2 | 0.5 | 32 | 5.5 | 5.9 | (55) | 5.0 | (45) |
| 3 | 300 | 4.8 | 4.2 | 0.5 | 29 | 6.2 | 5.2 | (47) | 5.8 | (53) |
| 4 | 300 | 4.8 | 4.2 | 0.5 | 35 | 3.0 | 6.6 | (57) | 5.1 | (43) |
| 5 | 300 | 4.8 | 4.2 | 0.5 | 32 | 5.5 | 10.4 | (96) | 0.5 | (4) |
| 6 | 300 | 4.8 | 4.2 | 0.5 | 20 | 10.7 | 5.2 | (50) | 5.3 | (50) |
| 7 | 300 | 4.8 | 4.2 | 0.5 | 40 | 1.0 | 6.6 | (58) | 4.7 | (42) |
| 8 | 450 | 0.5 | 27.6 | 0.5 | 30 | 5.0 | 6.9 | (63) | 4.0 | (37) |
| 9 | 450 | 0.5 | 27.6 | 1.0 | 32 | 3.4 | 9.2 | (96) | 0.4 | (4) |

TABLE 2-continued

| | 10 | 450 | 0.5 | 27.6 | 4.0 | 33 | 0.8 | 5.1 | (49) | 5.6 | (53) |
|---|---|---|---|---|---|---|---|---|---|---|---|

| Comparative Example | Catalyst composition Deposited alkali metals (per 100% of K$_2$CO$_3$) | | | Dimerization reaction conditions | | | Catalytic activity | | |
|---|---|---|---|---|---|---|---|---|---|
| | Na/K atomic ratio | Deposited alkali metals (total) ($\times 10^{-2}$ g-atom) | (g) | Temperature (°C.) | Pressure (kg/cm$^2 \cdot$ G) | LHSV (hr$^{-1}$) | Conversion (%) | Selectivity(*1) (%) | Half life (hr) |
| 1 | 24 | 10.9 | (2.6) | 150 | 100 | 2.70 | 7 | 8.4 | —(*2) |
| 2 | 1.2 | 10.9 | (3.3) | 150 | 100 | 2.70 | 22 | 93 | 5000 |
| 3 | 0.9 | 11.0 | (3.5) | 150 | 100 | 2.70 | 21 | 92 | 4800 |
| 4 | 1.3 | 11.7 | (3.5) | 150 | 100 | 2.70 | 21 | 92 | 4800 |
| 5 | 22 | 10.9 | (2.6) | 150 | 100 | 2.70 | 6 | 83 | —(*2) |
| 6 | 1.0 | 10.6 | (3.3) | 150 | 100 | 2.70 | 8 | 79 | —(*2) |
| 7 | 1.4 | 11.3 | (3.4) | 150 | 100 | 2.70 | 17 | 88 | 1800 |
| 8 | 1.7 | 10.9 | (3.2) | 150 | 100 | 2.70 | 9 | 80 | 600 |
| 9 | 26 | 9.6 | (2.3) | 150 | 100 | 2.70 | 5 | 82 | —(*2) |
| 10 | 0.9 | 10.7 | (3.4) | 150 | 100 | 2.70 | 17 | 88 | 1800 |

(*1): Proportion of 4-methyl-1-pentene in the hexene fraction.
(*2): Since the catalyst composition had low activity, their half periods were not measured.

What is claimed is:

1. A catalyst composition for dimerizing or codimerizing alpha-olefins consisting essentially of a molded article comprising an anhydrous inorganic potassium compound, and metallic sodium and metallic potassium dispersed on the surface of the molded article, said molded article further containing 0.7 to 3% by weight, based on the weight of the inorganic potassium compound, of elemental carbon, the atomic ratio of metallic sodium to metallic potassium being in the range of from 20:80 to 90:10 and the total proportion of metallic sodium and metallic potassium is 0.5–10% by weight based on the weight of the inorganic potassium compound.

2. The composition of claim 1 wherein the proportion of the elemental carbon is 0.8 to 2% by weight based on the weight of the inorganic potassium compound.

3. The composition of claim 1 wherein the elemental carbon is graphite.

4. The composition of claim 1 wherein the inorganic potassium compound is potassium carbonate.

5. The composition of claim 1 wherein the molded article has a pore volume ratio of 22 to 38% and a compression strength of 1.5 to 15 kg/cm$^2$.G, and is obtained by compression-molding a mixture of an elemental carbon powder and a powder of the inorganic potassium compound, said inorganic potassium compound powder having such a particle size distribution that it has an average particle diameter in the range of 150 to 600 microns and contains 1 to 15% by weight of particles having a particle diameter of less than 100 microns and 1 to 20% by weight of particles having a particle diameter of more than 600 microns.

6. The composition of claim 5 wherein the molded article is obtained by compression-molding a mixture of the elemental carbon powder and a powder of the inorganic potassium compound, said inorganic potassium compound powder having such a particle size distribution that it has an average particle diameter of 200 to 600 microns and contains 2 to 10% by weight of particles having a particle diameter of less than 100 microns and 2 to 15% by weight of particles having a particle diameter of more than 600 microns.

7. The composition of claim 5 wherein the molded article has a pore volume ratio of 26 to 33% and a compression strength of 2 to 10 kg/cm$^2$.G.

8. The composition of claim 1 wherein the atomic ratio of metallic sodium to metallic potassium is in the range of from 30:70 to 85:15.

9. The composition of claim 1 wherein the molded article is in the form of a tablet, a pellet or a sphere.

* * * * *